United States Patent [19]

Feld et al.

[11] 4,400,573
[45] Aug. 23, 1983

[54] MODIFICATION OF HYDROCARBON CONVERSION PROCESSES OVER CRYSTALLINE BOROSILICATE CATALYSTS BY ADDITION OF AN ALCOHOL OR ETHER

[75] Inventors: Raymond C. Feld, Winfield; Allen I. Feinstein, Wheaton, both of Ill.

[73] Assignee: Standard Oil Company (Indiana), Chicago, Ill.

[21] Appl. No.: 404,315

[22] Filed: Aug. 2, 1982

Related U.S. Application Data

[63] Continuation-in-part of Ser. No. 281,889, Jul. 9, 1981, abandoned.

[51] Int. Cl.³ ............................................... C07C 5/22
[52] U.S. Cl. .................................................... 585/481
[58] Field of Search ........................................ 585/481

[56] References Cited

U.S. PATENT DOCUMENTS 3,907,914  9/1975  Willis et al. .......................... 585/481
4,268,420  5/1981  Klotz .............................. 585/481 X

*Primary Examiner*—Paul F. Shaver
*Attorney, Agent, or Firm*—Wallace L. Oliver; William T. McClain; William H. Magidson

[57] ABSTRACT

Incorporation of above about 50 ppm alcohol or ether into feed of a hydrocarbon conversion process using an AMS-1B crystalline borosilicate-based catalyst alters the product distribution produced in such process.

14 Claims, No Drawings

MODIFICATION OF HYDROCARBON CONVERSION PROCESSES OVER CRYSTALLINE BOROSILICATE CATALYSTS BY ADDITION OF AN ALCOHOL OR ETHER

CROSS REFERENCE TO RELATED APPLICATIONS

This is a continuation-in-part to U.S. application Ser. No. 281,889, filed July 9, 1981, now abandoned.

BACKGROUND OF THE INVENTION

This invention relates to a process to convert alkyl-substituted aromatic compounds using a catalyst formed from crystalline borosilicate AMS-1B and more particularly relates to a method of isomerizing xylenes and converting ethylbenzene in which a desired product mix is obtained.

U.S. Pat. Nos. 4,268,420 and 4,269,813, incorporated by reference herein, disclose a use of crystalline borosilicate AMS-1B in a catalyst which simultaneously can isomerize xylenes and convert ethylbenzene. In commercial manufacture of para-xylene, typically a feed-stream containing $C_8$ aromatics (p-xylene, o-xylene, m-xylene and ethylbenzene) is used. From such stream p-xylene is removed, typically by crystallization or absorption, and the remaining mixture is contacted with a catalyst which isomerizes o-xylene and m-xylene to a mixture containing approximately a thermodynamic concentration of p-xylene. The isomerized mixture is recycled to the p-xylene removal unit. Within the process are units which remove by-products including fuel gases (such as ethane), benzene, toluene and heavy aromatics such as diethylbenzenes. Because of the difficulty of removing ethylbenzene from xylenes by distillation due to closeness of boiling points, it is desirable to convert ethylbenzene to other aromatic species by hydrodeethylation which mainly produces ethane and benzene or disproportionation/transethylation which mainly produces benzene, diethylbenzenes and dimethylethylbenzenes. A commercially useful catalyst for the isomerization of xylenes typically converts ethylbenzene.

It has been found that crystalline borosilicate AMS-1B formulated as a catalyst including an alumina matrix material and a catalytically-active metal such as molybdenum predominantly converts ethylbenzene through hydrodeethylation. Depending on the economic value of individual by-products from a para-xylene manufacturing unit, and the composition of the aromatics feedstream, sometimes it is advantageous to convert more ethylbenzene through a disproportionation/transethylation method. A process which permits a single catalyst composition to convert ethylbenzene by either the disproportionation/transethylation or hydrodeethylation methods would be useful. A process which permits rapid change from one conversion method to the other would be very advantageous.

SUMMARY OF THE INVENTION

In a process to convert hydrocarbons by contact of a hydrocarbon feed with an AMS-1B crystalline borosilicate based catalyst, the improvement comprising incorporating above about 50 ppm alcohol or ether into said feed.

BRIEF DESCRIPTION OF THE INVENTION

It has been discovered that incorporation of above about 50 parts per million by weight (ppm) alcohol or ether into an alkyl aromatic feed to a hydrocarbon conversion zone in which alkyl aromatics are converted using an AMS-1B crystalline borosilicate-based catalyst alters the products formed from such conversion.

The preferable hydrocarbon conversion process in which this invention is useful is a process to isomerize a mixture of xylenes while converting ethylbenzene to other hydrocarbon products. In such a process a mixture containing xylenes, usually deficient in para-xylene, and ethylbenzene is contacted with a catalyst composition such as one based on the crystalline borosilicate AMS-1B incorporated in a matrix material and impregnated with a molybdenum compound. The mixed xylenes, predominantly ortho- and meta-xylenes, are isomerized to a mixture containing para-xylene. The isomerized mixture preferably approximates a thermodynamic equilibrium mixture of xylenes which contains about 23.5 wt.% p-xylene, about 23.8 wt.% o-xylene and about 52.7 wt.% m-xylene. Simultaneous with the isomerization of xylenes, ethylbenzene is converted to other hydrocarbon products such as benzene, ethane, diethylbenzenes and ethylxylenes. A commercial process for the isomerization of xylenes and conversion of ethylbenzene typically contains 10 ppm or less of water.

In more detail the process of this invention is useful for liquid or vapor phase isomerization of xylenes and particularly the isomerization of mixed xylenes to para-xylene products. Operating conditions for the isomerization of a xylene feed broadly comprise a temperature of about 95° C. to about 540° C., a hydrogen-to-hydrocarbon mole ratio of about 0 to about 20, a weight hourly space velocity (WHSV) of about 0.01 weight unit of feed per hour per weight unit of catalyst ($hr.^{-1}$) to about 90 $hr.^{-1}$, and a pressure of about 0 psig to about 1000 psig. Advantageously, the conditions comprise a temperature of about 250° C. to about 480° C., a hydrogen-to-hydrocarbon mole ratio of about 1 to about 12, a WHSV of about 1 $hr.^{-1}$ to about 20 $hr.^{-1}$, and a pressure of about 0 psig to about 500 psig. The preferred conditions for the isomerization of xylenes comprise a temperature of about 315° C. to about 455° C., a hydrogen-to-hydrocarbon mole ratio of about 2 to about 8, a WHSV of about 1 $hr.^{-1}$ to about 10 $hr.^{-1}$, and a pressure of about 0 psig to about 300 psig. Typically, a feed to such process contains about 75 to 85 wt.% xylenes, about 10 to 15 wt.% ethylbenzene, about 0.2 to 1.0 wt.% paraffins and naphthenes, and about 0.5 to 5 wt.% $C_9+$ aromatics.

Although this invention is most useful in a xylene isomerization-ethylbenzene conversion process as described above, the invention can be used in other hydrocarbon conversion processes in which alteration of the method of conversion, and hence the products of such conversion, is desired.

In the process to convert ethylbenzene using an AMS-1B crystalline borosilicate-based catalyst impregnated with a molybdenum compound described herein in which water is not present in the feedstream, it is believed that hydrodeethylation is the predominant conversion method. In such method ethylbenzene, in the presence of hydrogen, is converted to benzene and ethane as represented by:

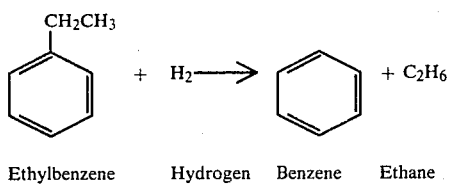

Ethylbenzene   Hydrogen   Benzene   Ethane

In the process using this invention in which water is present in the feed stream, a substantial method of ethylbenzene conversion is believed to be disproportionation between two molecules of ethylbenzene or a molecule of ethylbenzene and a molecule of xylene as represented by:

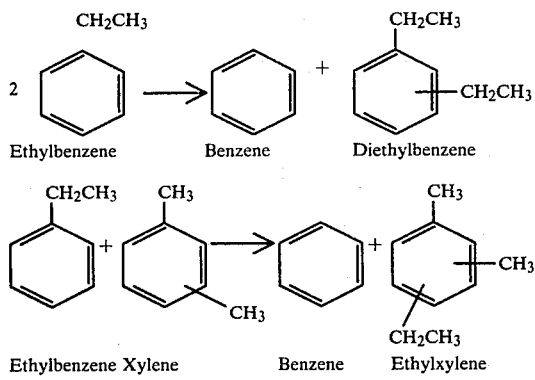

The feed to a xylene isomerization unit typically contains less than 10 parts per million (ppm) of water. It has been discovered that by adding an alcohol or an ether or a mixture thereof with water in a feed to a borosilicate-based isomerization catalyst system to above about 50 ppm and preferably about 100 to about 400 ppm, the by-product yield changes such that more $C_{10}$ aromatics are produced.

The amount of alcohol or ether usefully incorporated in a hydrocarbon feed according to this invention generally is above about 50 ppm. Preferably, the amount of alcohol or ether incorporated in a feed is about 100 to about 400 ppm although higher concentration of water can be used up to at least about 0.2 wt.%. In a xylene isomerization/ethylbenzene conversion process in which the method of this invention is used, alcohol or ether is incorporated in the feed before contact with the isomerization catalyst. Preferably, alcohol is used in this invention.

An advantage of the method of this invention is that the product mix from a hydrocarbon conversion can be altered reversibly by incorporation of alcohol or ether. Using the same isomerization catalyst, the product mix can be adjusted according to current requirements by addition or non-addition of alcohol or ether. Since alcohol or ether typically will not remain in such hydrocarbon conversion processes and will be removed by normal processing steps, interrupting alcohol or ether addition will cause the system to revert to an alcohol- and ether-free state and thus the resulting product mix will return to that experienced before alcohol or ether was added.

Alcohols useful in this invention can contain 1 to about 10 carbon atoms and include methanol, ethanol, n-propanol, isopropanol, n-butanol, isobutanol, t-butanol, phenol and the like. Glycols such as ethylene glycol also can be used. The preferred alcohol is methanol. The alcohols used in this invention can be mixed with water such that a mixture contains about 1 to about 100 wt.% alcohol. A typical alcohol/water mixture contains about 50 to 100 wt.% alcohol. Advantageously, a miscible alcohol/water mixture is used such as about 14 parts methanol per 1 part water.

Ethers useful in this invention can contain 1 to about 10 carbon atoms and include dimethyl ether, diethyl ether, isopropyl ether, diphenyl ether and the like. Other useful ethers include cyclic ethers or epoxides such as ethylene oxide, propylene oxide, tetrahydrofuran, dioxane and the like. The preferred ether is dimethyl ether. The ether used in this invention can be mixed with water such that a mixture contains about 1 to about 100 wt.% ether and typically contains about 50 to 100 wt.% ether.

Catalysts based on AMS-1B crystalline borosilicate incorporated in a binder and impregnated with a molybdenum compound, used in a xylene isomerization-ethylbenzene conversion process, convert ethylbenzene mainly by a hydrodeethylation mechanism. Typically, of the ethylbenzene converted about 40 to 90 percent is converted by hydrodeethylation with the remainder converted by disproportionation/transethylation. The amount of hydroeethylation activity in a specific AMS-1B borosilicate-based catalyst apparently depends in part on the amount and type of catalytically-active material placed onto the catalyst. The effect of incorporation of alcohol or ether in the feed to the conversion catalyst is to increase the proportion of ethylbenzene conversion by disproportionation/transethylation and to decrease the proportion of ethylbenzene conversion by hydrodeethylation. It has been observed that the greatest effect of alcohol or ether addition on conversion mechanism is found in catalysts which inherently convert primarily by hydrodeethylation.

The isomerization catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the x-ray diffraction pattern listed in Table I and by the composition formula:

$$0.9 \pm 0.2 M_{2/n}O:B_2O_3:ySiO_2:zH_2O$$

wherein M is at least one cation, n is the valence of the cation, y is between 4 and about 600, and z is between 0 and about 160.

TABLE I

| d-Spacing Å (1) | Assigned Strength (2) |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of a source of cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01 | 0.1–2 | 0.1–1 |
| $H_2O/OH^-$ | 10–4000 | 10–500 | 10–500 | where R is an organic compound and M is at least one cation having a valence n, such as an alkali metal or an alkaline earth metal cation.

By regulation of the quantity of boron (represented as $B_2O_3$) in the reaction mixture, it is possible to vary the $SiO_2/B_2O_3$ molar ratio in the final product.

More specifically, the material of the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blendor. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Useful cations in this invention include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0 \pm 0.2$ using a compatible base or acid such as sodium bisulfate or sodium hydroxide. After sufficient quantities of silicic acid polymer (Ludox) are added with intensive mixing, preferably the pH is again checked and adjusted to a range of about $11.0 \pm 0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°0 to 200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically-active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically-active ions include hydrogen, metal ions of Groups IB, IIB, IIIA and VIII, and ions of manganese, vanadium, chromium, uranium, and rare earth elements.

Also, water soluble salts of catalytically-active materials can be impregnated onto crystalline borosilicates used in this invention. Such catalytically-active materials include hydrogen, metals of Groups IB, IIB, IIIA, IVB, VB, VIB, VIIB, and VIII, and rare earth elements.

Ion exchange and impregnation techniques are well-known in the art. Typically, an aqueous solution of a cationic species is exchanged one or more times at about 25° to about 100° C. Impregnation of a catalytically-active compound on the borosilicate or on a composition comprising the crystalline borosilicate suspended in and distributed throughout a matrix of a support material such as a porous refractory inorganic oxide such as alumina, often results in a suitable catalytic composition. A combination of ion exchange and impregnation can be used. Presence of sodium ion in a composition usually is detrimental to catalytic activity. AMS-1B-based catalyst compositions useful in xylene isomerization can be prepared by ion exchange with nickelous nitrate and by impregnation with a molybdenum compound, such as ammonium molybdate. A catalyst composition which converts ethylbenzene substantially by hydrodeethylation is formed by impregnation with a molybdenum compound.

The amount of catalytically-active material placed on the AMS-1B borosilicate can vary from less than one weight percent to about thirty weight percent, typically from about 0.05 to about 25 weight percent, depending on the process use intended. The optimum amount can be determined easily by routine experimentation.

The AMS-1B crystalline borosilicate useful in this invention may be incorporated as a pure material in a catalyst or adsorbent, or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the aluminosilicate. Well-known materials include silica, silica-alumina, alumina, alumina sols, hydrated aluminas, clays such as bentonite or kaoline, or other binders well-known in the art. Typically, the borosilicate is incorporated within a matrix material by blending with a sol of the matrix material and gelling the resulting mixture. Also, solid particules of the borosilicate and matrix material can be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 2 wt.% to about 65 wt.% of such material.

Catalytic compositions comprising the crystalline borosilicate material of this invention and a suitable matrix material can be formed by adding a finely-divided crystalline borosilicate and a catalytically-active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically-active metal compound are distributed throughout the matrix material.

Specific details of catalyst preparations are described in U.S. Pat. No. 4,268,420.

This invention is demonstrated but not limited by the following Examples and Comparative Runs.

EXAMPLES I-VII

A crystalline borosilicate-based catalyst was prepared in a manner similar to that described in U.S. Pat. No. 4,269,813, and contained a molybdenum-impregnated AMS-1B crystalline borosilicate incorporated within an alumina binder. The total catalyst composition contained 80 wt.% alumina and 0.2 wt.% molybdenum. The AMS-1B crystalline borosilicate contained 0.5 wt.% boron and exhibited an x-ray diffraction spectrum similar to that described in Table I.

Twenty-five grams of AMS-1B crystalline borosilicate-based catalyst in the form of 1/16 inch extrudate were placed in a 0.5 inch inside diameter tubular reactor and pretreated with hydrogen at 1 SCF/hr at 454° C. and 250 psig for 2 hours, after which time the temperature was reduced to 385° C. and the hydrogen flow increased to about 3.5 SCF/hr while maintaining the system pressure at 250 psig. $C_8$ aromatic feed was introduced in the reactor at about 3.4 grams/minute on a once-through basis with no recycle. Both liquid and gaseous effluents were analyzed by gas chromatography. The amount of ethylbenzene converted by hydrodeethylation was calculated based on the following assumed transalkylation pathways:

Ethylbenzene + Xylenes → Dimethylethylbenzenes + Benzene

Ethylbenzene + Xylenes → Ethyltoluene + Toluene

2 Ethylbenzene → Diethylbenzenes + Benzene

Based on these pathways the amount of ethylbenzene converted by hydrodeethylation in percent equals the moles of ethylbenzene reacted minus the sum of the moles of ethylbenzene converted by such transalkylation pathways, all divided by the moles of ethylbenzene reacted and multiplied by 100. The results of these Examples are shown in Tables II and III while a Comparative Run in which only 10 ppm of water is present is shown in Table IV. A review of the data for Examples I-III and Comparative Run A shows presence of alcohol in the feed decreases the proportion of ethylbenzene converted by hydrodeethylation and increases the amount of $C_{10}$ aromatic by-products.

TABLE II

| | | Examples | | |
|---|---|---|---|---|
| Conditions | | I | | II |
| Methanol in Feed (ppm) | | 155 | | 78 |
| Temperature (°C.) | | 385 | | 385 |
| Pressure (psig) | | 250 | | 250 |
| Hydrogen/Hydrocarbon (molar ratio) | | 2.27 | | 2.16 |
| Space Velocity (WHSV) (hr$^{-1}$) | | 6.03 | | 6.05 |
| Components (wt. %) | Feed | | Feed | |
| Paraffins and Naphthenes | 1.93 | 1.96 | 1.94 | 2.15 |
| Benzene | 0.0 | 2.38 | 0.0 | 2.35 |
| Toluene | 1.43 | 2.20 | 1.42 | 2.17 |
| Ethylbenzene | 13.77 | 10.02 | 13.73 | 10.22 |
| p-Xylene | 7.94 | 17.88 | 7.81 | 18.09 |
| m-Xylene | 46.04 | 39.22 | 46.13 | 39.13 |
| o-Xylene | 22.75 | 16.98 | 22.79 | 16.99 |
| Ethyltoluenes | 1.38 | 1.30 | 1.39 | 1.29 |
| Trimethylbenzenes | 0.56 | 0.89 | 0.56 | 0.84 |
| Diethylbenzenes | 1.64 | 2.03 | 1.64 | 2.01 |

TABLE II-continued

| | Examples | | | |
|---|---|---|---|---|
| Dimethylethyl-benzenes | 2.47 | 4.98 | 2.54 | 4.61 |
| Tetramethylbenzenes | 0.08 | 0.18 | 0.06 | 0.16 |
| Results | | | | |
| Ethylbenzene conversion (%) | | 27.1 | | 25.6 |
| p-Xylene Approach to Equilibrium (%) | | 104 | | 106 |
| Ethylbenzene Conversion by Hydrodeethylation (%) | | 31 | | 37 |

TABLE III

| | Examples |
|---|---|
| Conditions | III |
| t-Butanol in Feed (ppm) | 1200 |
| Temperature (°C.) | 385 |
| Pressure (psig) | 250 |
| Hydrogen/Hydrocarbon (molar ratio) | 2.18 |
| Space Velocity (WHSV) (hr$^{-1}$) | 6.07 |

| Components (wt. %) | Feed | |
|---|---|---|
| Paraffins and Naphthenes | 1.82 | 2.10 |
| Benzene | 0.17 | 2.26 |
| Toluene | 1.40 | 2.28 |
| Ethylbenzene | 13.70 | 10.07 |
| p-Xylene | 7.77 | 17.64 |
| m-Xylene | 46.16 | 39.08 |
| o-Xylene | 22.76 | 16.87 |
| Ethyltoluenes | 1.40 | 1.37 |
| Trimethylbenzenes | 0.56 | 0.89 |
| Diethylbenzenes | 1.66 | 2.15 |
| Dimethylethylbenzenes | 2.48 | 5.08 |
| Tetramethylbenzenes | 0.12 | 0.23 |
| Results | | |
| Ethylbenzene conversion (%) | | 26.6 |
| p-Xylene Approach to Equilibrium (%) | | 103 |
| Ethylbenzene Conversion by Hydrodeethylation (%) | | 22 |

TABLE IV

| | Comparative Run A |
|---|---|
| Conditions | |
| Water in Feed (ppm) | 10 |
| Alcohol in Feed (ppm) | 0 |
| Temperature (°C.) | 385 |
| Pressure (psig) | 250 |
| Hydrogen/Hydrocarbon (molar ratio) | 2.11 |
| Space Velocity (WHSV) (hr$^{-1}$) | 6.91 |

| Components (wt. %) | Feed | |
|---|---|---|
| Paraffins and Naphthenes | 1.89 | 2.18 |
| Benzene | 0.0 | 1.52 |
| Toluene | 1.00 | 1.61 |
| Ethylbenzene | 9.41 | 7.52 |
| p-Xylene | 7.68 | 19.05 |
| m-Xylene | 52.17 | 43.57 |
| o-Xylene | 22.06 | 18.45 |
| Ethyltoluenes | 1.05 | 0.84 |
| Trimethylbenzenes | 1.09 | 1.28 |
| Diethylbenzenes | 0.92 | 0.84 |
| Dimethylethylbenzenes | 2.69 | 3.08 |
| Tetramethylbenzenes | 0.05 | 0.06 |

TABLE IV-continued

| | Comparative Run A |
|---|---|
| Results | |
| Ethylbenzene conversion (%) | 20.1 |
| p-Xylene Approach to Equilibrium (%) | 99 |
| Ethylbenzene conversion by Hydrodeethylation (%) | 86 |

What is claimed is:

1. In a process to convert alkyl-substituted aromatic hydrocarbons by contact of an alkyl-substituted aromatic hydrocarbon feed with an AMS-1B crystalline borosilicate-based catalyst incorporated within a matrix material and on which is impregnated a molybdenum compound, the improvement comprising incorporating above about 50 ppm alcohol or ether into the alkyl-substituted aromatic hydrocarbon feed.

2. The improvement of claim 1 wherein the process to convert hydrocarbons is a process to convert ethylbenzene and the hydrocarbon feed is a mixture comprising xylenes and ethylbenzene.

3. The improvement of claim 1 wherein about 50 to about 2,000 ppm alcohol or ether is incorporated into the feed.

4. The improvement of claim 2 wherein about 100 to 400 ppm alcohol or ether is incorporated into the feed.

5. The improvement of claim 1 wherein the AMS-1B crystalline borosilicate-based catalyst is incorporated within an alumina matrix.

6. The improvement of claim 1 wherein an alcohol is incorporated into the hydrocarbon feed.

7. The improvement of claim 1 wherein an ether is incorporated into the hydrocarbon feed.

8. The improvement of claim 6 wherein the alcohol is methanol.

9. The improvement of claim 1 wherein the alcohol or ether is incorporated into the hydrocarbon feed as a mixture with water.

10. The improvement of claim 1 wherein the conversion conditions comprise a temperature of about 95° to about 540° C., a hydrogen-to-hydrocarbon molar ratio of 0 to about 20, a weight hourly space velocity of about 0.01 hr$^{-1}$ to about 90 hr$^{-1}$, and a pressure of about 0 psig to about 1,000 psig.

11. The improvement of claim 2 wherein the conversion conditions comprise a temperature of about 250° to about 480° C., a hydrogen-to-hydrocarbon molar ratio of about 1 to about 12, a weight hourly space velocity of about 1 hr$^{-1}$ to about 20 hr$^{-1}$, and a pressure of about 0 psig to about 500 psig.

12. The improvement of claim 2 wherein the conversion conditions comprise a temperature of about 315° C. to about 455° C., a hydrogen-to-hydrocarbon molar ratio of about 2 to about 8, a weight hourly space velocity of about 1 hr$^{-1}$ to about 10 hr$^{-1}$, and a pressure of about 0 psig to about 300 psig.

13. The improvement of claim 10, 11 or 12 wherein about 100 to 400 ppm alcohol or ether is incorporated into the feed.

14. The improvement of claim 2, 11 or 12 wherein the hydrocarbon feed comprises about 75 to 85 weight percent xylenes and about 10 to 15 weight percent ethylbenzene.

* * * * *